United States Patent [19]

Nankai et al.

[11] Patent Number: 5,185,256
[45] Date of Patent: Feb. 9, 1993

[54] METHOD FOR MAKING A BIOSENSOR

[75] Inventors: Shiro Nankai; Mariko Kawaguri; Takashi Iijima, all of Osaka, Japan

[73] Assignee: Matsushita Electric Industrial Co., Ltd., Japan

[21] Appl. No.: 774,129

[22] Filed: Oct. 15, 1991

Related U.S. Application Data

[60] Continuation of Ser. No. 428,680, Oct. 30, 1989, abandoned, which is a division of Ser. No. 27,204, Feb. 20, 1987, Pat. No. 4,897,173.

[30] Foreign Application Priority Data

Jun. 21, 1985 [JP] Japan .................................. 60-136423
Nov. 7, 1985 [JP] Japan .................................. 60-249203
Nov. 7, 1985 [JP] Japan .................................. 60-249204
Dec. 11, 1985 [JP] Japan .................................. 60-278202
Apr. 2, 1986 [JP] Japan .................................. 61-75728

[51] Int. Cl.$^5$ ...................... C12N 11/00; C12M 1/40
[52] U.S. Cl. .................... 435/174; 435/288; 435/817
[58] Field of Search ............... 156/153, 154; 204/416, 204/415, 412, 403, 153.12; 435/817, 288, 25, 174; 436/807; 427/372.2, 113, 122

[56] References Cited

U.S. PATENT DOCUMENTS

| | | | |
|---|---|---|---|
| 1,771,236 | 7/1930 | Schellenger | 427/122 X |
| 4,356,074 | 10/1982 | Johnson | 204/403 |
| 4,454,007 | 6/1984 | Pace | 204/403 |
| 4,545,382 | 10/1985 | Higgins et al. | 204/415 |
| 4,655,880 | 4/1987 | Lin | 204/403 |
| 4,711,245 | 12/1987 | Higgins et al. | 204/415 |
| 4,945,045 | 7/1990 | Forrest et al. | 204/403 X |
| 4,963,245 | 10/1990 | Weetall | 204/403 |

FOREIGN PATENT DOCUMENTS

| | | | |
|---|---|---|---|
| 0127958 | 12/1984 | European Pat. Off. | 204/403 |
| 59-166852 | 9/1984 | Japan | 204/403 |

OTHER PUBLICATIONS

Taylor et al., "Solvents, Oils, Resins and Driers", *Paint Technology Manuals*, Chapman & Hall (1961), pp. 11–12.
Gardner et al, "Paints, Varnishes, Lacquers and Colors", *Paint Testing Manual*, Gardner Laboratory, Inc. (Mar., 1962) pp. 359–363 and 473–475.
Handbook of Printing Engineering, published by Giho-Do (1983).
Product Information, Acheson Japan, Ltd., available on Feb. 1985 from Acheson Industries, Inc.
Duffy, Printing Inks Developments Since 1975, Noyes Data Corporation (1979), pp. 194, 196, 324 and 325.

*Primary Examiner*—Jeff H. Aftergut
*Attorney, Agent, or Firm*—Lowe, Price, LeBlanc & Becker

[57] ABSTRACT

This invention relates to a biosensor which comprises an insulative base, an electrode system formed on the substrate and primarily made of carbon, and a perforated body having an enzyme and an electron acceptor and integrally combined with the electrode system whereby a concentration of a specific component in a biological liquid sample can be electrochemically measured rapidly and accurately by a simple procedure of mere addition of the liquid sample. Several simple biosensors for measuring a specific component in a liquid sample are known including a sensor of the type in which a change of a dye formed by an enzyme reaction is optically detected and a sensor of the type using an enzyme electrode. These sensors, respectively, involve an interference with colored matters in liquid sample and necessity of washing of an electrode system every measuring procedure. In addition, the sensors are complicated in structure and materials therefor are expensive. In the present invention, the electrode system is formed mainly of carbon and is integrally combined with the perforated body, so that washing of the electrode system is unnecessary. Thus, an inexpensive, simply-operated biosensor of the disposable type can be provided.

3 Claims, 6 Drawing Sheets

METHOD FOR MAKING A BIOSENSOR

This application is a continuation application of application Ser. No. 07/428,680, filed Oct. 30, 1989, now abandoned, which is a divisional application of application Ser. No. 07/027,204, filed Feb. 20, 1989 now U.S. Pat. No. 4,897,173.

TECHNICAL FIELD

This invention relates to a biosensor for quantitatively determining specific components in various biological samples accurately, rapidly and simply and also to a method for making the same.

TECHNICAL BACKGROUND

In recent years, a variety of biosensors have been developed using specific catalytic actions of enzymes, and their applications to the clinical and examining field have been attempted. As inspection items and specimens are now increasing, there is a demand for biosensors which permit rapid and accurate measurements.

With a sensor for glucose, for instance, since diabetics are drastically increasing in number, the measurment and control of blood-sugar levels by hitherto employed procedures in which the blood is centrifugated to obtain plasma and subjected to the measurement, takes a relatively long time. Thus, a sensor of the type which enables one to measure it with the whole blood is now required. In the simplest form, there is known a sensor which includes, similar to a urine test paper, a support and a carrier formed on the support and containing an enzyme reacting only with glucose and a dye which undergoes a change at the time of the enzyme reaction or with a product formed during the enzyme reaction. The blood is added to the carrier, and a change of the dye after a certain period of time is measured visually or optically. However, this system is disadvantageous in that colored matters in the blood greatly interfere with the measurement, resulting in a low accuracy.

In order to overcome the above, there has been proposed a multi-layered carrier for analysis as is particularly shown in FIG. 1 (Japanese Laid-Open Utility Model Application No. 54-178495). This carrier includes a transparent support 1, on which are superposed a reagent layer 2, a developing layer 3, a waterproof layer 4 and a filtration layer 5 in this order. When a blood sample is dropped from the above, solid matters in the blood such as red blood cells, platelets and the like, are initially removed by means of the filtration layer 5, followed by uniform infiltration from a small hole 6 of the waterproof layer 4 toward the developing layer 3. At the reagent layer 2, the reaction is caused to proceed. After completion of the reaction, light is applied from the direction of the arrow through the transparent support 1 to measure a substrate concentration by spectroscopy. As compared with the known simple stick carrier, this carrier has a complicated structure but the removal of blood cells is more improved. However, it takes a long time for the infiltration and the reaction of the blood corpuscles, so that the waterproof layer 4 for preventing the sample from drying is essential, with an attendant problem that the equipment and the carrier become complicated.

On the other hand, a biosensor of the type as shown in FIG. 2 has been proposed (for example, in Japanese Laid-open Patent Application No. 59-166852) as a system in which a specific component in a biological sample is quantitatively determined in high accuracy without resorting to any procedures such as dilution of a liquid sample and agitation. The biosensor includes an insulative substrate 7, a measuring electrode 8 and a counter electrode 9, which have, respectively, leads 10, 11, embedded in the substrate 7, and a perforated body 12 which covers exposed portions of these electrodes and carries an oxydo-reductase and an electron acceptor. When the liquid sample is dropped on the perforated body, whereupon the oxydo-reductase and the electron acceptor in the perforated boy dissolve in the sample liquid, thus permitting the enzyme reaction with a substrate in the liquid sample to proceed. As a result, the electron acceptor is reduced. After completion of the enzyme reaction, the reduced electron acceptor is electrochemically oxidized and a concentration of the substrate in the liquid sample is determined from a current for the oxidation.

In this arrangement, although the measurement can be performed simply by replacing the perforated body every measurement, additional procedures, such as washing, are undesirable for the electrode system. If parts including the electrodes could be disposably replaced whenever the measurement is effected, the measuring product would become very simple but the system would be very expensive in view of the electrode materials such as platinum and the arrangement. Although the platinum electrodes may be formed by a sputtering method or a vacuum evaporation method, they are still expensive in view of the manufacture.

In order to measure a specific component in a biological sample such as blood simply, rapidly and in high accuracy, a desirable type of sensor is one which can yield measurements only by addition of a liquid sample to the sensor without dilution or weighing. In addition, a sensor of the disposable type is also desirable which does not involve any procedures such as washing, sampling and the like.

DISCLOSURE OF THE INVENTION

A biosensor according to the invention is of the type which comprises an insulative base and an electrode unit or system comprising, at least, a measuring electrode and a counter electrode and in which an oxydoreductase, an electron acceptor and a liquid sample are reacted with one another and a variation in concentration of a substance occuring during the reaction is electrochemically detected by means of the electrode system to determine a concentration of a substrate in the sample liquid. In this biosensor, the electrode system is made primarily of carbon and is covered with a perforated body carrying an oxydo-reductase and an electron acceptor therein so that the electrode system and the base are integrally constituted. The electrode surface has been preliminarily coated with a protein, so that an influence of proteins in samples, such as blood, on the electrodes by adsorption can be mitigated. Once the carbon electrodes have been subjected to a heat treatment in a predetermined temperature range, the electrodes become stabilized with respect to electrochemical activity or states on the exposed portions, thereby improving storage stability. Moreover, when the electrode system and the base are formed integrally with not only the perforated body having an oxydo-reductase and an electron acceptor, but also a sample addition layer, a filtration layer and a liquid-retaining layer, one can cause the enzyme reaction with a substrate in liquid sample and the electrode reaction of the electron acceptor to proceed more smoothly.

According to the invention, there is provided a biosensor of the disposable type including a disposable electrode system, by which a substrate concentration in a sample liquid, e.g. a glucose concentration in the blood, can be measured by a simple procedure of adding the liquid sample, in a rapid and highly accurate fashion without dilution and weighing.

BEST MODE FOR CARRYING OUT THE INVENTION

Example 1

Figure 1:
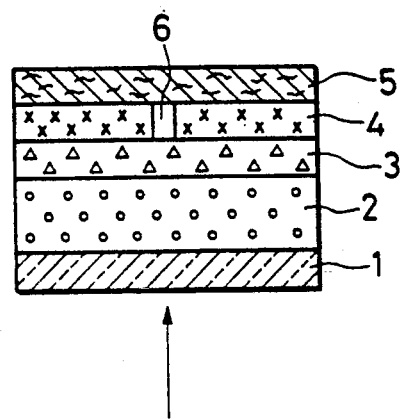
FIG. 1 is a schematic view of a known sensor for glucose.
Figure 2:
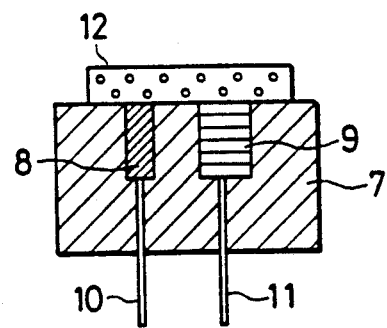
FIG. 2 is a schematic view of a known sensor for glucose using an enzyme electrode.
Figure 3:
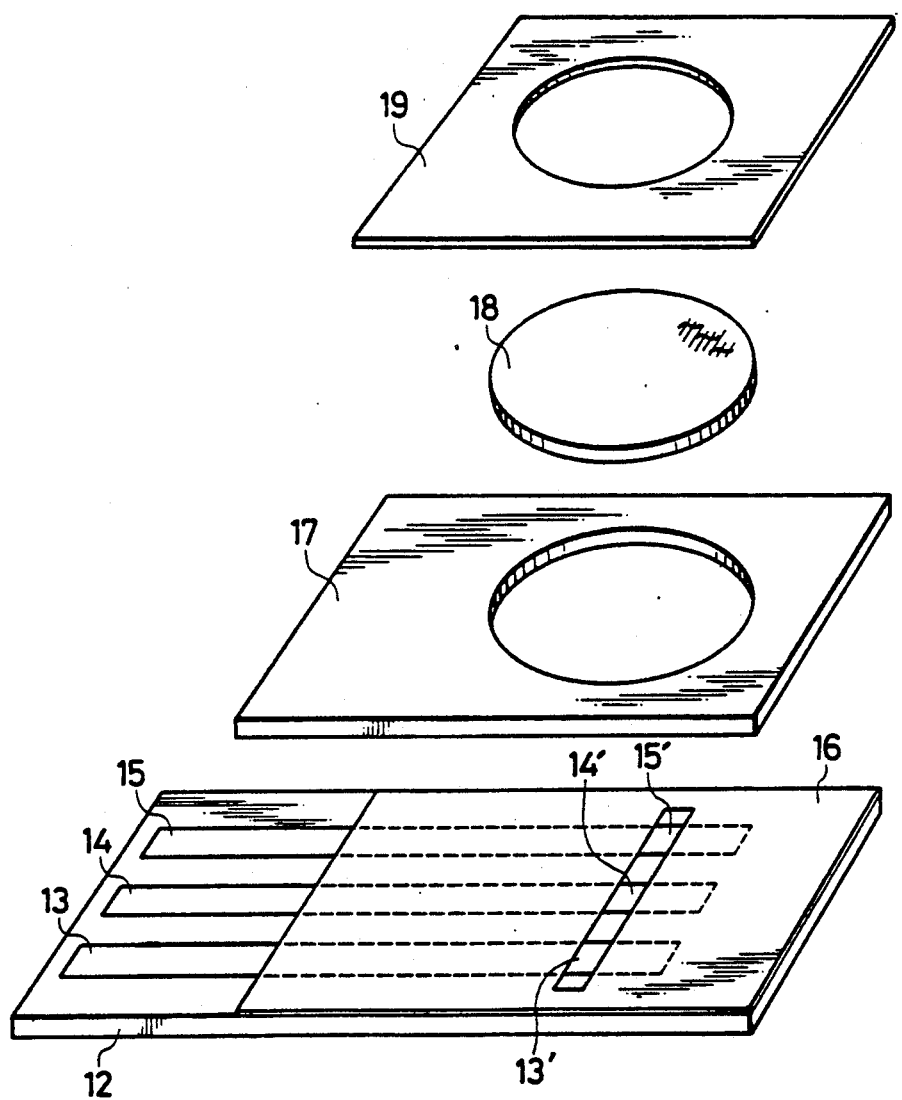
FIG. 3 is a schematic view of a biosensor according to one embodiment of the invention.

A sensor for gluscose is described as one embodiment of a biosensor. FIG. 3 shows one embodiment of a sensor for glucose and is an exploded view for constituent parts. A conductive carbon paste containing a resin binder is printed, by screen printing, on an insulative base 12 made of polyethylene terephthalate in the form of parallel stripes, followed by heating for drying to form an electrode system consisting of a counter electrode 13, a measuring electrode 14 and reference electrode 15. The electrode system is partially covered, after which an insulative paste mainly composed of a polyester is printed in the same manner as described above while leaving portions 13', 14' and 15' (each 1 mm$^2$ in area) of the respective electrodes acting as electrochemical sites, followed by heating to form an insulative layer 16. Subsequently, the exposed portions 13', 14' and 15' are polished and subjected to heat treatment in air at 100° C. for 4 hours.

Figure 4:
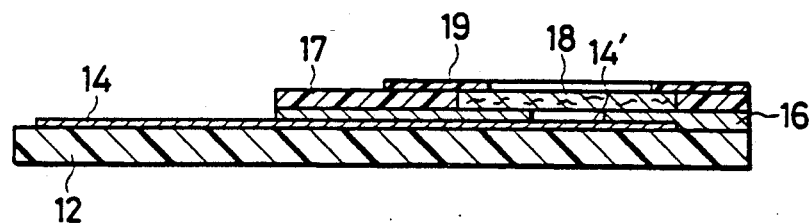
FIG. 4 is a longitudinal section of the biosensor shown in FIG. 3.

Thereafter, a punched holding frame 17 of a synthetic resin such as a polyester is adhered to the insulative layer 16. A perforated body 18 having an enzyme and an electron acceptor is placed in the hole of the frame 17 so that the electrodes 13', 14' and 15' are completely covered. A resin cover 19 having an opening which is smaller than the outer diameter of the perforated body 18 is adhered, thereby obtaining an integrally assembled sensor. The sectional view of this biosensor taken along the measuring electrode 14 is shown in FIG. 4. The perforated body used above is fabricated as follows: a nylon non-woven fabric is provided as a base; the base is dipped in a solution of 200 mg of glucose oxidase as an oxydo-reductase and 400 mg of potassium ferricyanide as an electron acceptor dissolved in 1 ml of a phosphate buffer solution containing 0.25 wt % of a surface active agent (polyethylene glycol alkylphenyl ether) and having a pH of 5.6 and immersed in ethanol containing 0.25 wt % of a surface active agent for crystallization; and the thus immersed base is dried under reduced pressure to obtain a perforated material.

A glucose standard solution provided as a liquid sample was dropped in the perforated body of the thus fabricated sensor. Two minutes after the dropping, a pulse voltage of 700 mV based on the reference electrode was applied, by which the measuring electrode was polarized anodically.

In this case, the added glucose reacts with potassium ferricyanide by the action of the glucose oxidase contained in the perforated body 18 to form potassium ferrocyanide. Upon the application of the pulse voltage for the anodic polarization, a current for the oxidation in proportion to a concentration of the formed potassium ferrocyanide is obtained. This current value corresponds to concentration of the glucose substrate.

Figure 5:
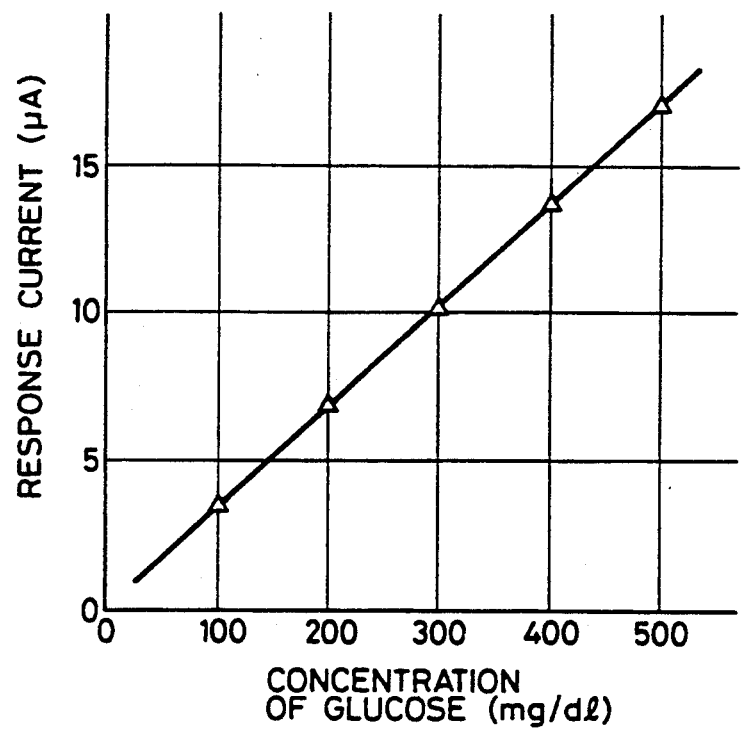
FIGS. 5, 6 and 7 are, respectively, response characteristics of the biosensor shown in FIG. 3.

FIG. 5 shows the relation between a current obtained 20 seconds after application of the voltage and a glucose concentration as one of response characteristics of the sensor, revealing a very good linearity

EXAMPLE 2

Figure 6:
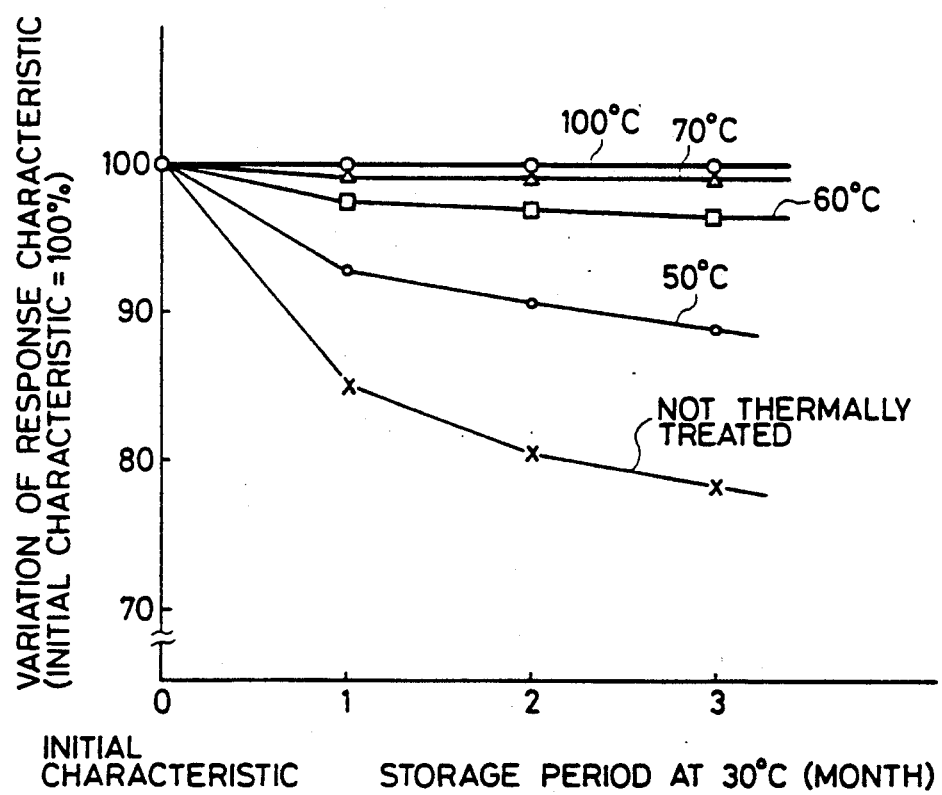

The procedure for fabricating the sensor for glucose as described in Example 1 was repeated except that the thermal treatment after polishing of the carbon electrodes was effected at 100° C., 70° C. and 50° C., and that the heat treatment was not effected, thereby fabricating a plurality of sensor for each case. These sensos were kept at 30° C. and their variation in response to the glucose standard solution was determined. FIG. 6 shows a variation of a response current relative to an initial response current taken as 100% for the sensor using the electrodes thermally treated at different temperatures. As will be clearly seen from the figure, the variation of the response accompanied by the storage is not so great when the treating temperature is 60° C. or higher. However, such a variation is great for 50° C. and also for the non-treatment. This is considered to result from the fact that the exposed surface portion of the polished carbon printed electrodes is not stabilized. When the electrode surface was not polished, a response current was about ⅓ of that of polished electrodes. The difference in response current between the polished and non-polished electrodes is considered to be attributed to partial covering of the carbon surface with a resin component contained as a binder in the paste. Polishing can remove the resin binder from the carbon electrode surface and can uniformly smooth the electrode surface. In addition, the heat treatment at temperatures not lower than 60° C., preferably 60°-170° C. for 1-8 hours permits the the exposed electrodes portion to become stabilized.

According to our experiments, when the heat treatment was effected at a temperature of 70°-150° C. for 4 hours, good results were obtained in that the variation in response current after storage was very small.

Good results cannot be obtained when the heat treatment is effected at temperatures not higher then 50° C. as discussed above. On the contrary, the heat treatment at temperatures higher than 170° C. should rather be avoided because the polyethylene terephthalate substrate of the sensor tends to undergo thermal deterioration and the resin binder in the carbon paste is apt to deteriorate.

EXAMPLE 3

Similar to the procedure described in Example 1, electrodes were formed on an insulative base and, after polishing. were thermally treated at 100° C. for 4 hours. Thereafter, an aqueous solution of albumin (50 mg/ml) was dropped over the surface of the electrode portions 13', 14' and 15' and allowed to stand for 5-10 minutes, followed by washing with water to remove an excess of the albumin and drying. By the above procedure, the albumin was adsorbed on the respective electrode surfaces.

After formation of the electrode system partially covered with the albumin, sensors for glucose were made in the same manner as in Example 1.

Figure 7:
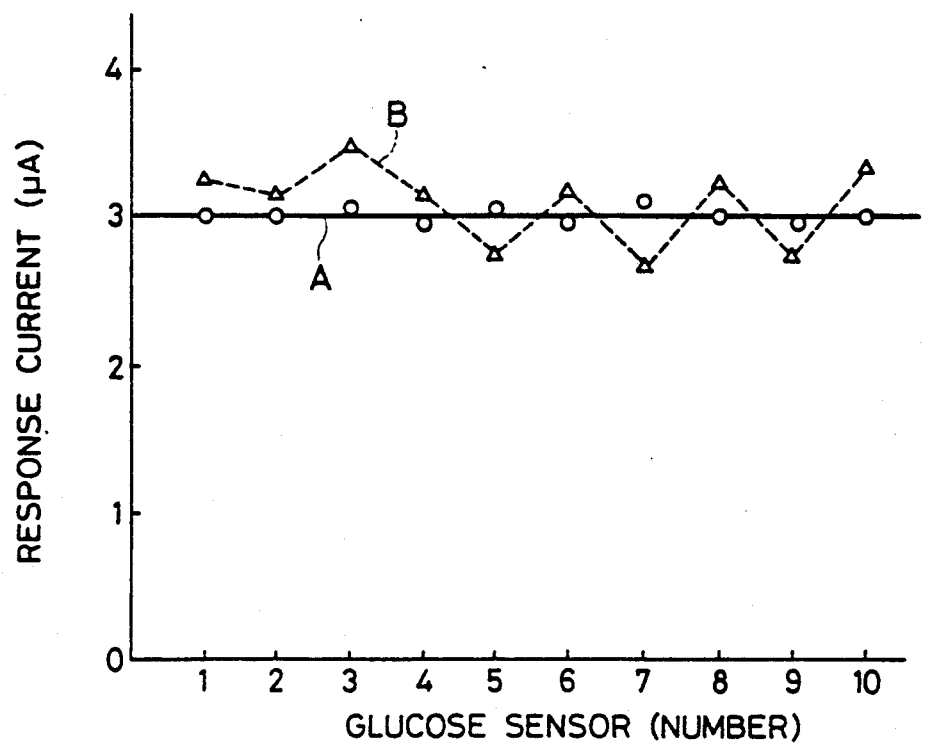

A serum sample containing about 90 mg/dl of glucose was dropped in position of the 10 glucose sensors fabricated above. After 2 minutes, a pulse voltage of 700 mV was applied for measurement in the same manner as in Example 1. Good reproducibility was attained as shown in A in FIG. 7. On the other hand, glucose sensors were fabricated in the same manner as described above but using electrodes not subject to adsorption with albumin. These sensors were subjected to measurement in the same manner as set forth above. As shown in B in FIG. 7, the variation of the response current is greater than that of A. A and B are both indicative of the response current for 10 glucose sensors fabricated in the same manner, but the difference in reproducibility depending on the adsorption treatment is considered to ascribe to the difference in absorbability of adsorbates, such as proteins, in the serum sample on the electrodes. As seen from A, the electrodes adsorbing sufficiently with albumin can prevent the response current from scattering.

Instead of albumin, an aqueous solution of glucose oxidase (100 mg/ml) was used for the treatment in the same manner as described above, with the result that the response characteristic of a high reproducibility was obtained.

The proteins to be absorbed should not be construed as limiting to albumin and glucose oxidase used in the above example. If at least measuring electrode among the electrodes is subjected to the adsorption treatment, similar results are obtained.

EXAMPLE 4

Figure 8:
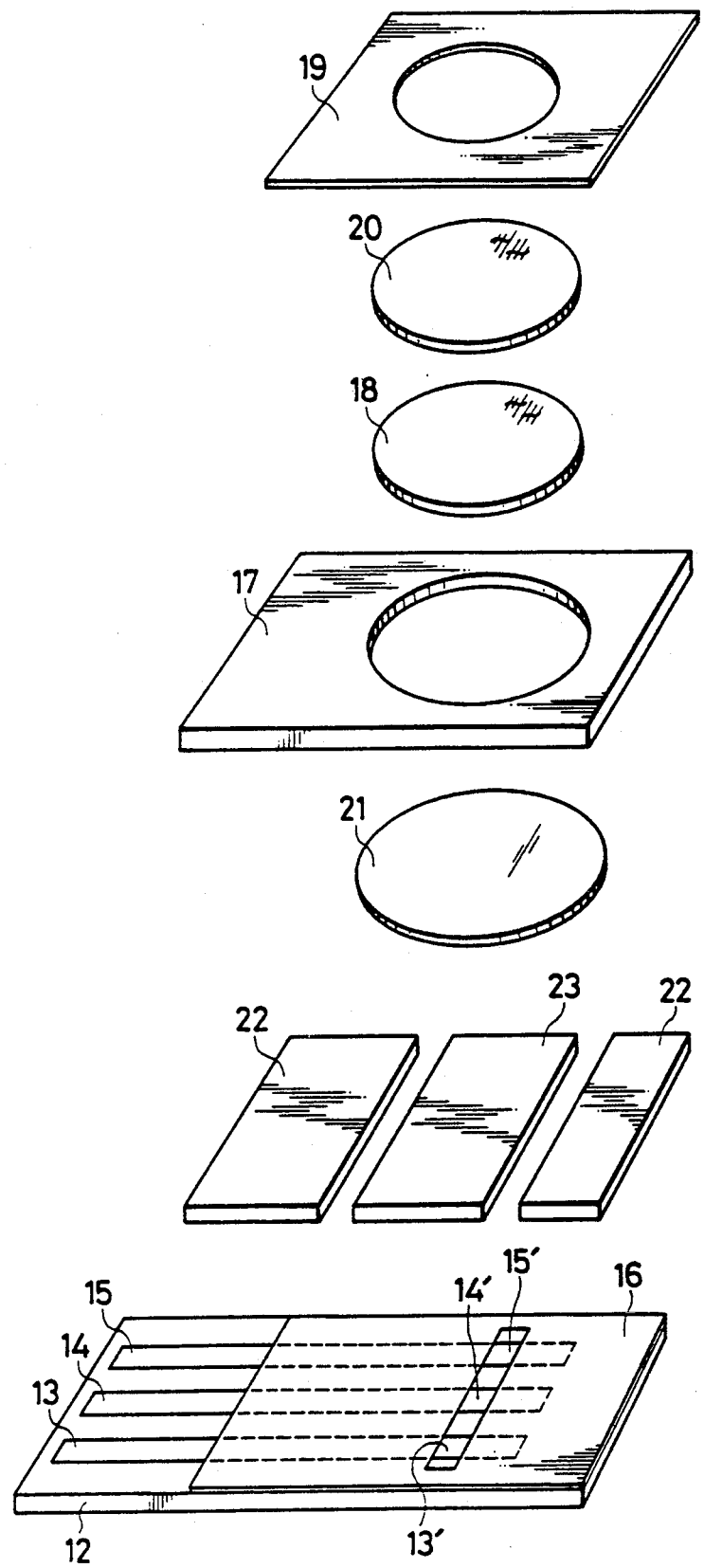
FIG. 8 is a schematic view of a biosensor according to another embodiment of the invention.
Figure 9:
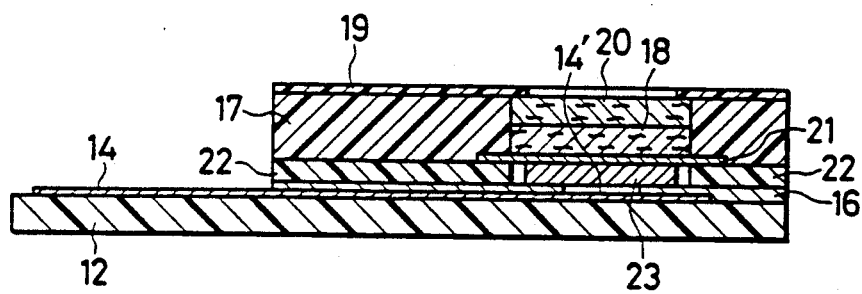
FIG. 9 is a longitudinal section of the biosensor shown in FIG. 8.

In the same manner as in Example 3, an albumin-coated electrode system was formed on an insulative base. FIG. 8 shows an exploded view of a sensor prior to assembling. A liquid-retaining layer 23 made of a perforated rayon non-woven fabric is placed, while controlling the height by means of two resin plates 22 serving as a spacer, in order to cover an electrode system therewith. Then, a filtration layer 21 made of a polycarbonate film and having a pore size of 1 um is mounted on the layer 23 and fixed with a holding frame 17. An enzyme and electron acceptor-bearing perforated body 18 and a sample addition layer 20 made of a cellulose non-woven fabric, both in the form of a disk, are placed in the hole of the holding frame 17. A resin cover having an opening which has a diameter smaller than the outer diameters of the perforated disk body 18 and the sample addition layer is adhered, thereby obtaining an integral combination. A sectional view of the thus integrally combined biosensor taken along the measuring electrode 1 is shown in FIG. 9.

In the same manner as in Example 1, glucose oxidase and potassium ferricyanide were incorporated in the perforated disk body 18. Glucose sensors using this perforated body 18 were fabricated. The blood (whole blood) was added to each sensor, whereupon it was rapidly spread over and through the entire surface of the sample addition layer 20. While the enzyme and potassium ferricyanide in the perforated body 18 were being dissolved in and permitted to react with the blood, red cells were filtered by means of the filtration layer 21. The resultant filtrate alone was absorbed in the liquid retaining layer 23, allowing a reaction solution to be collected on the electrode portions 13', 14' and 15' in an amount enough to cause the electrode reaction to proceed. In this manner, the glucose in the blood reacted in the same manner as in Example 1 and a concentration of the glucose could be detected through the electrode system.

It will be noted that the technique of integral assembling of a biosensor of the invention is not limited to those shown in the examples with respect to the shape and combination of the frame, the cover and the like.

The types of materials for the liquid-retaining layer, the sample addition layer and the filtration layer are not limited to those shown in the examples, but any materials which meet the purposes of the invention may be used.

On the other hand, reference has been made to, in the above examples, the three-electrode system, but the measurement would be possible using a two-electrode system consisting of a counter electrode and a measuring electrode.

As for the electrode acceptor incorporated in the perforated body 18, the potassium ferricyanide used in the examples is convenient because the reaction proceeds stably. On the other hand, p-benzoquinone is suitable for high-speed measurement because of the high reaction rate. Alternatively, 2,6-dichlorophenol indophenol, methylene blue, phenazine methosulfate, potassium beta-naphthoquinone-4-sulfonate and the like may also be used.

The sensors described in the examples may be applied not only to glucose, but also to systems relating to oxydo-reductases, for example, as an alcohol sensor, a cholesterol sensor of the like. Glucose oxidase has been used as an oxydo-reductase, but other enzymes such as, for example, alcohol oxidase, xanthine oxidase, cholesterol oxidase and the like may also be used.

INDUSTRIAL UTILITY

The biosensor of the invention can be used to measure a specific component in various biological liquid samples rapidly, accurately and simply and has a very high utility in clinical examinations.

What is claimed is:

1. A method for making a biosensor which comprises providing an insulating base, applying a carbon paste onto said base in a pattern form to form an electrode system including at least a measuring electrode and a counter electrode, polishing, after drying of the carbon paste, the surfaces of the electrode system, making the electrodes stable for electrochemical activity by subjecting the polished electrode system to a thermal treatment at a temperature of from 60° to 170° C. for 1 to 8 hours, covering the electrode system with a perforated body having an oxidoreductase and electron acceptor therein, and integrally combining said perforated body with said electrode system and said insulating base.

2. A method according to claim 1, wherein said carbon paste is printed on said insulating base.

3. A method according to claim 2, wherein the thermal treatment is effected at a temperature of from 70° to 150° C. for 4 hours.

* * * * *